US00PP07974P

United States Patent [19]

Lyrene

[11] Patent Number: Plant 7,974

[45] Date of Patent: Sep. 15, 1992

[54] HIGHBUSH BLUEBERRY—MARIMBA CULTIVAR

[75] Inventor: Paul M. Lyrene, Gainesville, Fla.

[73] Assignee: University of Florida, Gainesville, Fla.

[21] Appl. No.: 639,469

[22] Filed: Jan. 10, 1991

[51] Int. Cl.[5] ..... A01H 5/00

[52] U.S. Cl. ..... Plt./33.1

[58] Field of Search ..... Plt./33

*Primary Examiner*—James R. Feyrer

*Attorney, Agent, or Firm*—Saliwanchik & Saliwanchik

[57] ABSTRACT

Description and specifications of a new and distinct highbush blueberry variety which originated from seed produced by a hand-pollinated cross between two Florida blueberry selections is provided. The new blueberry variety can be distinguished by its low chilling requirement, its early ripening, disease-resistant bush, firm fruit, and small dry picking scar.

1 Drawing Sheet

SUMMARY OF THE INVENTION

The new and distinct variety of highbush blueberry originated from a hand pollinated cross between two Florida highbush blueberry selections made in 1974 at the Florida Agricultural Experiment Station experimental greenhouse in Gainesville, Fla. The seeds from this controlled hybridization were germinated in a greenhouse during the winter of 1974–1975. Resulting seedlings were planted in the spring of 1975 in an experimental plot at Earleton, Fla. The seedlings fruited in the spring of 1977 and one, designated FL 77-3, was selected for its outstanding fruit quality and low chilling requirement.

During 1977, the original plant selection was propagated asexually by rooting softwood cuttings, and a test planting of three plants was established. In 1985 the clone was again propagated by softwood cuttings and a 15-plant plot was established in 1986 at the Florida Agricultural Experiment Station Horticultural Unit at Gainesville, Fla. The new variety has been asexually propagated by softwood cuttings on at least four other occasions. It roots readily from softwood cuttings. During asexual multiplication, the vegetative and fruit characteristics of the original plant have been maintained.

Bushes of the new variety are medium in vigor and upright in growth. The plant produces enough basal shoots to renew the plant as it ages, but it is not a heavy sprouter. The plant produces a large number of flower buds, but the number of flower buds is not excessive if the plant is grown on favorable soils. The variety has shown no signs of delayed flowering or fruiting, even following winters in which fewer than 300 hours of temperatures below 7° C. were recorded.

Plants of the new variety appear to be moderate to high in resistance to cane canker incited by *Botryosphaeria corticus*. They appear to be normal or above normal in resistance to Phytophthora root rot, stem blight, Botrytis blight, and fungi which cause defoliation in the fall.

Plants of the new variety have a very low chilling requirement. Average date of 50% anthesis is 6 days before Georgiagem and 8 days after Sharpblue. Average date of 50% harvest for the new variety is May 7, five days later than for Sharpblue and one day later than for Georgiagem. The average date of the first harvest from the new variety will be about May 1 in north-central Florida. Fruit of the new variety are medium in size, averging 1.6 g per berry. Color is dark blue with a moderately heavy waxy coating. Both the stem scar and the firmness are excellent, and the fruit detach readily from the plant when ripe. These last three characteristics should make the new variety a good candidate for mechanical harvest for the fresh market. Flavor is good and similar to Sharpblue.

The new variety has been named the Marimba variety.

BRIEF DESCRIPTION OF THE PHOTOGRAPHS

The accompanying photographs show typical specimens of the fruit and leaf of the new variety in color as nearly true as it is reasonably possible to make in a color illustration of this character.

DETAILED DESCRIPTION OF THE NEW VARIETY

The following is a detailed description of the pomological characteristics of the subject blueberry. Where dimensions, sizes, colors, and other characteristics are given, it is to be understood that such characteristics are approximations of averages set forth as accurately as practicable.

The description reported herein is from specimens grown at Gainesville, Fla.

Plant:

*Size.*—Medium.

*Time of* 50% *anthesis.*—February 22.

*Growth.*—Medium in vigor, cessation of growth in early October. Plant more upright than spreading.

*Productivity.*—Medium. Young plants precocious.

*Cold hardiness.*—Plant and dormant flower buds hardy to below −13° C. Flowers and fruits hardy to −2° C.

*Chilling requirement.*—The plant requires only about 200 hours duration of temperatures at or below 7° C. to induce normal leafing and flowering in the spring.

*Stems.*—Moderately upright. Readily produces new sprouts sparingly from the base.

*Internode length.*—1.2 cm. Color of 1-year-old stems — red-pink. Color of current-season stems — green-pink.

*Disease resistance.*—Moderate resistance to Phytophthora root rot, stem blight, powdery mildew, Botrytis flower blight, cane canker, and various defoliating leaf diseases.

Foliage:

*Leaves.*—Color — mature leaves green to blue-green. Leaf margins are entire. Leaves glabrous on both surfaces. Leaves average 22 mm wide × 38 mm long.

Flowers:

*Date of 50% anthesis.*—February 22.

*Flower color.*—White.

*Flower bud number.*—Medium to high.

The variety has moderately high self-incompatibility

Fruit:

*Maturity.*—First harvest May 1. Mid harvest May 7.

*Size of berry.*—Medium. Average weight 1.60 g.

*Berry color.*—Dark blue, with moderate surface wax.

*Fruit stem scar.*—Very small and dry.

*Berry firmness.*—Good.

*Berry flavor and texture.*—Flavor sweet with moderate acid level. Skins of normal thickness and seeds of normal size for a cultivated highbush blueberry.

*Storage quality.*—Good.

*Uses.*—Primarily for shipment to fresh fruit markets. Would also be suitable for customer-pick marketing and for processing.

*Suitability for mechanical harvest.*—Medium to good.

The variety: The most distinctive features of the variety are its low chilling requirement, disease resistance, excellent berry stem scar, and good firmness.

I claim:

1. A new and distinct variety of highbush blueberry, substantially as illustrated and described, characterized by its low chilling requirement, disease-resistant bush, early ripening fruit, firm berry, small dry fruit scar, and easy detachment from the plant.

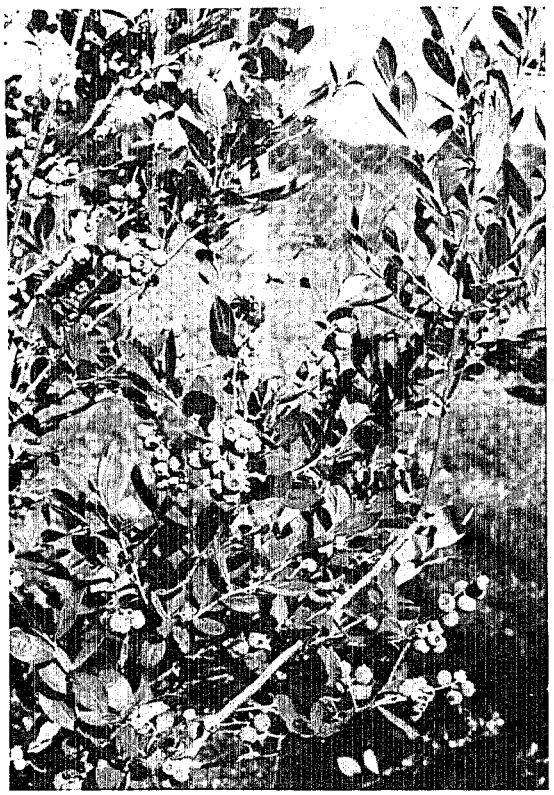
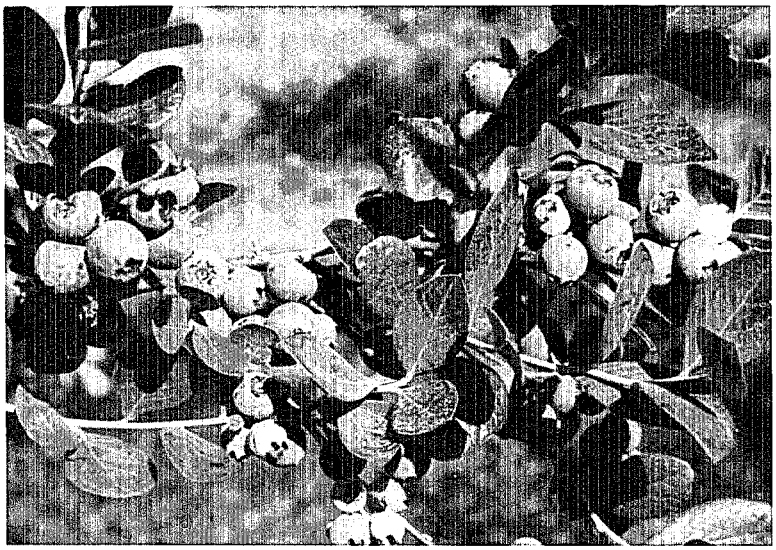

* * * * *